US012303142B2

(12) United States Patent
Vouaux et al.

(10) Patent No.: US 12,303,142 B2
(45) Date of Patent: May 20, 2025

(54) INTRAMEDULLARY TIBIA ALIGNMENT SYSTEM

(71) Applicant: Aesculap AG, Tuttlingen (DE)

(72) Inventors: Alexis Vouaux, Poulangy (FR); Christophe Girouard, Sarcicourt (FR)

(73) Assignee: Aesculap AG, Tuttlingen (DE)

( * ) Notice: Subject to any disclaimer, the term of this patent is extended or adjusted under 35 U.S.C. 154(b) by 392 days.

(21) Appl. No.: 18/009,803

(22) PCT Filed: Jun. 16, 2021

(86) PCT No.: PCT/EP2021/066300
§ 371 (c)(1),
(2) Date: Dec. 12, 2022

(87) PCT Pub. No.: WO2021/255122
PCT Pub. Date: Dec. 23, 2021

(65) Prior Publication Data
US 2023/0218306 A1    Jul. 13, 2023

(30) Foreign Application Priority Data

Jun. 19, 2020 (EP) ..................... 20181194

(51) Int. Cl.
*A61B 17/15* (2006.01)
(52) U.S. Cl.
CPC ................... *A61B 17/157* (2013.01)
(58) Field of Classification Search
CPC .................................... A61B 17/157
See application file for complete search history.

(56) References Cited

U.S. PATENT DOCUMENTS

| 5,342,368 A | 8/1994 | Petersen |
| 2009/0264890 A1 | 10/2009 | Duggineni et al. |
| 2012/0101504 A1* | 4/2012 | Habegger ............ A61B 17/157 606/88 |

(Continued)

FOREIGN PATENT DOCUMENTS

JP    2009006066 A    1/2009

OTHER PUBLICATIONS

Office Action received in Japanese Application No. 2022-578782 dated Dec. 6, 2024, with translation, 7 pages.

(Continued)

*Primary Examiner* — Samuel S Hanna
(74) *Attorney, Agent, or Firm* — Christopher A. Rothe; CM Law (57) ABSTRACT

An intramedullary tibia alignment system includes an alignment rod, a tibial resection guide and a tibial alignment jig. The tibial alignment jig has a sliding rail, a casing slidably receiving the sliding rail and being attached to the alignment rod, and a user adjustment element rotatably held by the alignment rod. The user adjustment element is functionally connected to the casing by a link element such that a rotation is converted into a pivoting movement. The user adjustment element and the alignment rod are adapted to interlock with each other at a plurality of rotational positions of the user adjustment element. The plurality of rotational positions correspond to different orientations of the alignment rod in accordance with the pivoting movement of the alignment rod.

13 Claims, 3 Drawing Sheets

(56) References Cited

U.S. PATENT DOCUMENTS

2013/0158556 A1  6/2013  Jones et al.

OTHER PUBLICATIONS

Search Report received in Japanese Application No. 2022-578782 dated Dec. 18, 2024, translation, 17 pages.
Search Report received in European Application No. 20181194.0-1122 dated Nov. 18, 2020, 7 pages.
Search Report received in International Application No. PCT/EP2021/066300 dated Sep. 9, 2021, 3 pages.
Written Opinion received in International Application No. PCT/EP2021/066300 dated Sep. 9, 2021, 5 pages.

* cited by examiner

INTRAMEDULLARY TIBIA ALIGNMENT SYSTEM

CROSS-REFERENCE TO RELATED APPLICATIONS

This application is the United States national stage entry of International Application No. PCT/EP2021/066300, filed Jun. 16, 2021, and claims priority to European Application No. 20181194.0, filed Jun. 19, 2020. The contents of International Application No. PCT/EP2021/066300 and European Application No. 20181194.0 are incorporated by reference herein in their entireties.

FIELD

The invention concerns joint arthroplasty, especially knee arthroplasty and total knee arthroplasty. More specifically, the invention concerns devices which enable the surgeon to efficiently and accurately resect proximal tibial portions prior to placing prostheses thereon. In particular, the invention relates to an intramedullary tibia alignment system.

BACKGROUND

The knee joint enables a person's leg to flex or articulate during movement. At the knee, a lower bone (tibia) meets an upper bone (femur). Proximate the knee, the femur has two projections known as femoral condyles. Femoral condyles engage fibrocartilage at the upper end of the tibia. The knee joint is held together by ligaments, capsule, muscle, and tendons. Four ligaments are especially prominent in knee structure, with one ligament on either side of the knee and two ligaments in the center. Of the center ligaments, one ligament is oriented toward the front and one toward the back. The patella or knee cap is a piece of bone supported in front of the knee joint. Functionally, the patella acts as a shield.

The knee joint may be rendered nearly or totally inoperative by extended and heavy use, disease, or trauma. Often, the best therapy is total replacement (arthroplasty). During total knee arthroplasty, the femoral and tibial surfaces joined at the knee are totally replaced. The first step in this process is the removal of the condylar surfaces and some underlying portions thereof. The distal end of the femur is resected to provide clearance for a femoral prosthetic component. Similarly, a proximal portion of the tibia is resected to provide a relatively flat surface for a tibial prosthetic component.

A person's weight is transferred from the head of the femur proximate the hip to the ankle. Proper alignment of the knee must be maintained when femoral and tibial prosthetic devices are installed to allow the proper transfer of weight to continue. In order for the prostheses to function properly, femoral and tibial surfaces arising from these resections must be correctly aligned. These surfaces must also be the proper distance apart so that the planned prostheses will fit and function properly.

Alignment of tibial resection guides prior to surgical resection has traditionally been done by using a long straight metal rod. One end of the metal rod is aligned with the center of the femoral head. The other end is aligned with the center of the ankle. The center of the femoral head is determined either from an X-ray or, less preferably, estimated by establishing a point located the width of three fingers medial to the superior iliac spine. When aligned, the rod should bisect the center of the knee components and should be generally perpendicular to a tibial and femoral resection plane. Arthritic knees may have varus or valgus deformities and corresponding bone defects or gaps.

Resection planes in which these defective portions are exposed may not be satisfactory for supporting replacement prostheses. Presently, the surgeon must either install a prosthetic device over a resected bone with an exposed defective gap and fill the defect under the component with bone cement or a spacer, for example, or resect the tibia still farther away from the knee to remove the defect or gap and insert a thicker prosthetic component. If the surgeon makes a further resection, a tibial resection guide is needed to ensure that the resected portion is the correct shape and size.

For example, the US 2009/264890 A1 discloses a tibia alignment system for aligning a proximal tibial resection cutting instrument, the tibia alignment system having an alignment rod, a tibial resection guide and a tibial alignment jig for orientating the tibial resection guide relative to the alignment rod and thus relative to a tibia, wherein the tibial alignment jig has a sliding rail adapted to be connected to a head of the tibia at its proximal end portion, and a casing slidably receiving the sliding rail along a sliding axis.

SUMMARY

Thus, there may be a need for an intramedullary tibia alignment system which enables the surgeon to quickly and efficiently align a tibial resection guide so that installed prostheses will fit and operate correctly. In particular, there may be need for an intramedullary tibia alignment system enabling to more precisely adjust the position and orientation of the tibial resection guide.

The intramedullary tibia alignment system described herein may apply to "Total Knee Replacement", a surgical procedure wherein planar surfaces and/or curvilinear surfaces must be created in or on bone to allow for proper attachment or implantation of prosthetic devices. In Total Knee Replacement, a series of planar and/or curvilinear surfaces, or "resections," are created to allow for the attachment of prosthetic or other devices to the femur, tibia and/or patella.

The intramedullary tibia alignment system according to the invention has an alignment rod for adjusting the alignment system individually to a tibia. The intramedullary tibia alignment system further has a tibial resection guide (also named as cutting block) for guiding a separate (external) cutting instrument (which does not belong to the system) at a correct position and inclination with respect to the tibia and which is connected or connectable to a proximal end portion of the alignment rod. Preferably, such an alignment rod is a telescopic extending bar being adjustable to individual patient's tibias of different length.

The intramedullary tibia alignment system also has a tibial alignment jig for orientating the tibial resection guide relative to the tibia. The tibial alignment jig is connected to the alignment rod proximal to the tibial resection guide. The tibial alignment jig has a sliding rail adapted to be connected to a head of the tibia at its proximal end portion. The tibial alignment jig has a casing slidably receiving a distal end portion of the sliding rail. The casing is attached to the alignment rod via a pivoting axis (extending perpendicular to the rod) such that the alignment rod and the sliding rail are kept pivotable to each other around the pivoting axis.

According to the invention, the tibial alignment jig has a user adjustment element, for example a Vernier adjustment element, rotatably held by the alignment rod and functionally connected to the casing preferably by a link element such that a rotation of the user adjustment element relative to the alignment rod is converted into a pivoting movement of the alignment rod relative to the sliding rail. The user adjustment element and the alignment rod are adapted to interlock with each other at a plurality of rotational positions of the user adjustment element, which plurality of rotational positions correspond to different orientations of the alignment rod relative to the tibia in accordance with the pivoting movement of the alignment rod.

In other words, according to the invention, an intramedullary alignment system is provided comprising a (telescopic) rod/bar and a cutting block for guiding a separate cutting instrument (saw) is connected to a proximal end portion of the rod. Furthermore, an inclination-adjustment device (alignment jig) is provided at the proximal end of the rod (proximal to the cutting block) for adjusting the angle/inclination of the cutting block relative to the tibia.

For this, the inclination-adjustment device comprises a cantilever arm (sliding rail) the proximal end portion of which is adapted to be fixed at the tibia, especially a head of the tibia wherein the distal end portion thereof is supported in/at a casing/bracket to be slidable in its longitudinal direction. The casing/bracket is pivotably held at the proximal end portion of the rod (proximal to the cutting block) via a pivoting axis which is orientated perpendicular to the longitudinal axis of the rod. Accordingly, the rod is pivotable around the pivoting axis relative to the cantilever arm, thereby changing the angle/orientation relative to the tibia.

According to the invention, it is intended to implement a user adjustment means/element/mechanism being adapted to provide a fine-tuning adjustment of the inclination of the rod (and therefore of the cutting block) relative to the tibia. Preferably, the user adjustment element may have a knoplike shape or a knop-like shape portion for providing grip for the user while turning the user adjustment element. In other words, for this purpose a manually actuatable turning knop/sleeve/bolt is provided which is rotatably supported/held/mounted at/on/in the alignment rod (preferably parallel to the rod). The turning sleeve is functionally connected with the casing (preferably inside the casing) such that a rotation of the turning sleeve around its longitudinal axis is converted into a pivoting movement of the casing around the pivoting axis.

Preferably, a locking mechanism can be provided. The locking mechanism may be adapted to lock and unlock rotatable movement between the alignment rod and the user adjustment element (in a fine-tuning manner). The locking mechanism may comprise a release element, preferably a snap-fit hook, fixed to the user adjustment element and an engaging element, preferably a snap-fit slot, fixed to the alignment rod. The release element engages with the engaging element in a locking position.

More preferably, the locking mechanism may comprise a plurality of engaging elements each forming a locking position. The plurality of engaging elements may be distanced from each other, preferably in a circumferential direction of the alignment rod. The circumferential direction of the alignment rod corresponds to the circumferential direction of the user adjustment element. More preferably, the plurality of engaging elements may be distanced from each other such that two adjacent locking positions generate a constantly stepwise, more preferably in 1° steps, pivoting movement between the alignment rod and the sliding rail. That is, turning the user adjustment element form one locking position to an adjacent locking position causes a pivoting movement which corresponds to change of the orientation of the tibial resection guide relative to the tibia of 1° in sagittal view. That is, the pivoting movement corresponds to the posterior slope of the resection. In other words, in addition a (preferably manually operable) lock mechanism may be provided between the turning sleeve/bolt and the rod which is split in or which comprises a plurality of locking positions being distanced from each other in turning direction of the turning sleeve/bolt wherein in a preferred embodiment of the invention the circumferential distance between two adjacent locking positions is defined to generate a 1° pivoting of the rod relative to the cantilever arm. Thus, the pivoting movement can smoothly adjust the posterior tibial slope. More preferably, the user adjustment element may comprise a scale indicating the adjusted slope corresponding to the chosen locking position.

In a particularly preferred embodiment according to the invention, the release element may comprise a button on a circumference of the user adjustment element, which is adapted to be pressed manually by a user to unlock the locking mechanism, preferably to disengage the engagement in one of the locking positions, and to enable the user adjustment element to be turned in clockwise or anticlockwise in circumferential direction of the alignment rod. That is, the locking mechanism is manually releasably engaged. Thus, unintentional adjustment can be avoided.

More preferably, the locking mechanism may be designed to provide an adjustability of the orientation of at least 0° to 7°. In a preferred embodiment, the locking mechanism may comprise a limit stop limiting the adjustability of the turning of the user adjustment element, and thus, the adjustable slope within a predetermined range, in particular, a predetermined range corresponding to a slope of 0° to 7°.

In a preferred embodiment according to the invention, the casing may comprise a sliding guiding slot slidably receiving the sliding rail along the sliding axis, the sliding axis being a longitudinal direction/axis of the sliding rail. For example, the sliding guiding slot may be a through hole extending through the casing in the sliding direction/along the sliding axis. Thus, a compact configuration can be provided. For example, the sliding guiding slot may have a rectangular cross section (in a plane perpendicular to the sliding axis) precluding any degree of freedom of the sliding rail relative to the casing except for the relative movement in the sliding direction. In other words, the casing, in particular the sliding guiding slot, provides a linear bearing/one-directionally bearing for the sliding rail.

Preferably, the sliding rail may comprise a hole elongated along the sliding axis through which the alignment rod passes. The elongated hole may be designed so as to allow maximal pivoting movement of the alignment rod relative to the casing and/or to allow maximal sliding movement of the sliding rail relative to the casing while staying attached to the casing. Thus, the slidability is not impeded by the alignment rod and the pivotability is not impeded by the sliding rail.

In a preferred embodiment of the invention, the casing may comprise a pivoting element attaching the casing pivotably to the alignment rod via the pivoting axis, the pivoting axis being perpendicular to the rotational axis and perpendicular to the sliding axis. Because the axes (pivoting axis, sliding axis, rotational axis) are perpendicular to each other, any orientation can be adjusted. Preferably, the pivoting element may contact a circumferential surface of the user adjustment element (or the alignment rod). Thus, the pivoting movement is guided and can be controlled. Preferably, the pivoting element may be fixed to the casing, in particular, to an inner side of the casing to extend towards the circumferential surface of the user adjustment element.

More preferably, the pivoting element may be formed by two (first) pins, the longitudinal axis of the pins each corresponding to the pivoting axis and the pins being arranged on circumferentially opposite sides of the user adjustment element.

In a preferred embodiment of the invention, the user adjustment element may comprise a pivoting guiding groove in a circumferential surface of the user adjustment element receiving the link member. The link member may be fixed at the inner side of the casing and extending towards the pivoting guiding groove. The pivoting guiding groove may be designed to cause a relative movement of the casing relative to the user adjustment element along a longitudinal axis/direction of the link member in case the user adjustment element is rotated. Preferably, the longitudinal axis of the link member corresponds to the sliding axis, that is, is axially parallel to the sliding axis. Thus, the conversion between the rotation of the user adjustment element relative to the alignment rod and the pivoting movement of the alignment rod relative to the sliding rail can be achieved. This has the advantage of easily adjusting the posterior tibial slope by turning/rotating the user adjustment element.

In other words, the pivoting function can be achieved by a link member being fixed at an inner side of the casing to extend towards the circumferential surface of the turning sleeve/bolt wherein the turning sleeve/bolt comprises a guiding slot receiving/slidingly holding the free end of the link member which guiding slot extends in the circumferential direction of the turning sleeve/bolt and is designed to draw and/or to pull the link member and, therefore, the casing towards/away from the turning sleeve/rod in case the turning sleeve/bolt is (manually) rotated.

In a preferred embodiment, the pivoting guiding groove have a depth, preferably constantly, increasing or decreasing along its circumferential extension. Due to the varying depth of the pivoting guiding groove the link member is drawn/pulled to and/or pushed away from the alignment rod and the user adjustment element, that is, closer to or further away from the user adjustment element (and thus, the alignment rod causing the pivoting movement). In an alternative preferred embodiment, the pivoting guiding groove may have a helical form, preferably with a constant pitch. That is, a connection between a spherical axis (of the link member) and a helical groove guiding the link member causes the pivoting movement. For example, a length of the groove can be limited to less than half a circumferential length of the cylindrical support. In particular, the length may be limited to an angle/slope to be adjusted in accordance with the tibial resection guide.

In a preferred embodiment of the invention, a fastening element may be provided for rotatably attaching the user adjustment element to the alignment rod. The user adjustment element may comprise a groove in a circumferential surface of the user adjustment element receiving the fastening element being fixed to the alignment rod. The groove rotatably supports the alignment rod and the user adjustment element to each other. The groove may be arranged in a plane perpendicular to the rotational axis. For example, the fastening element may be formed by one or a plurality of (second) pins, the longitudinal axis of the pins each being perpendicular to the rotational axis and the pins being spaced in a circumferential direction of the user adjustment element (and the alignment rod), more preferably in equal distances. The groove is formed circumferentially. Thus, relative rotatability can be provided while preventing any other relative movement, for example, a translation along the rotational axis, between the alignment rod and the user adjustment element.

In a preferred embodiment of the invention, the alignment rod may be a telescopic extending bar being adjustable in length. Thus, the alignment rod may be adapted to the patient's individual tibia length. Further, the telescopic alignment rod extending from the end of the adjustments offers the possibility to verify a chosen angulation. In an alternative preferred embodiment of the invention, the alignment rod and the user adjustment element may each form a through hole extending along the longitudinal direction of the alignment rod, that is, the rotational direction, the through hole adapted to receive a (separate) extramedullary check rod. Thus, the chosen angulation can be verified with the extramedullary check rod going through the system. Hence, the verifying is more accurate than a system comprising an extramedullary check rod outside of the system.

Preferably, a tibial adjustment housing may be provided, the tibial adjustment housing holding the alignment rod and connecting the alignment rod and the tibial alignment jig with the tibial resection guide. More preferably, the tibial adjustment housing may be slidably attached to the alignment rod along the rotational axis. Consequently, the tibial adjustment housing can enable the tibial resection guide to move in a direction of the alignment rod. Thus, a tilt and shift movement of the tibial resection guide can be achieved by the intramedullary tibia alignment system as described herein.

In other words, summing up, the invention relates to an intramedullary tibia alignment system that allows easily adjusting the posterior slope from 0° to 7° with a 1° increment before performing a tibia resection, during a total knee arthroplasty. The adjustment of the posterior slope allows managing the flexion of the knee joint. The intramedullary tibia alignments may have usually the disadvantage that it does not have a possibility to adjust and lock the angle of the posterior slope but only some fixed angles. The intramedullary system may allow positioning the tibial cutting guide, needed for tibia resection, with the tibia intramedullary can now as reference. Moreover, the system may allow, by unlocking and turning the button, to orientate the cutting guide support. This orientation may be from 0° to 7° with 1° increment in the sagittal view (posterior slope). The posterior slope may be between the two extreme positions 0° and 7°. In particular, the system may allow an adjustment and a locking of the angle, which does not take up much space. In more other words, the sliding rail may allow the connection with the intramedullary axis and the displacement of the system. The angulation of the slope from 0° to 7° is managed by the rotation of the system around the axis, in solidarity with the sliding nut. This rotation may be generated by the handling of a button. Indeed, the rotation of the button may generate an angulation of the system according to the connection between the spherical axis and the helical groove of the cylindrical support. The required angle can be locked according to the spring part of the release button which may come and strike the, for example 8, specific grooves (0° to 7°) of the support and, after that, the angle of the system cannot be changed without an action of the user on the release button. A new angle can be chosen only by pushing the release button and turn the button until the appropriate groove. In these other words, the button may be referred to the rotary knob, as described above. In parallel and/or at the end of all the adjustments, the system offers the possibility to verify the chosen angulation with an extra medullary check by including through an alignment rod. The rod is going through the system, so the system is more accurate than a system with a shift, where the rod is outside of the mechanism.

BRIEF DESCRIPTION OF THE DRAWINGS

The invention is explained in more detail below on the basis of a preferred embodiment using figures. The figures are of a schematic nature and intended to improve the understanding of the invention. Same elements are referenced to with the same reference signs.

DETAILED DESCRIPTION

FIGS. 1 to 5 show a preferred embodiment of an intramedullary tibia alignment system 1 (hereinafter referred to as alignment system 1) according to the invention. The alignment system 1 is for aligning a (tibial resection) cutting instrument relative to a tibia 2. The alignment system 1 guides the adjustment of the tibial resection cutting instrument to achieve a desired posterior slope of the resection of the tibia 2.

The alignment system 1 has an alignment rod/alignment pipe 3 for adjusting the alignment system 1 individually to a tibia 2. The alignment system 1 has a tibial resection guide 4 for guiding the cutting instrument. The tibial resection guide 4 is connected to a distal (lower) end portion of the alignment rod 3. The alignment system 1 has a tibial alignment jig 5 for orientating the tibial resection guide 4 relative to the tibia 2. The tibial alignment jig 5 fixes the alignment rod 3 statically to the tibia 2 of a patient. The tibial alignment jig 5 is connected to the alignment rod 3 proximal (above in FIG. 1) to the tibial resection guide 4.

Figure 1:
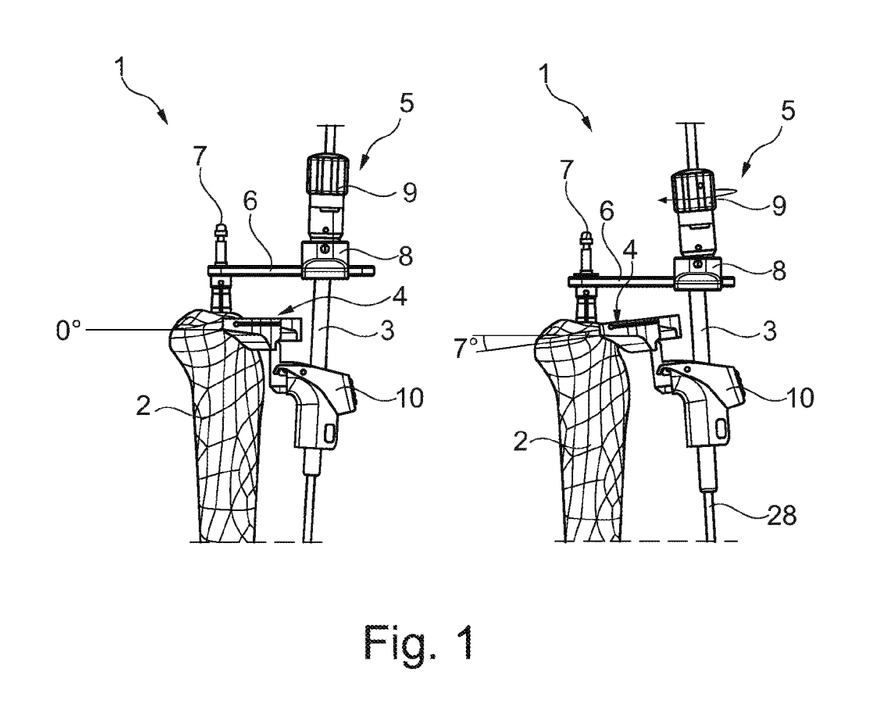
FIG. 1 illustrates a perspective view of an intramedullary tibia alignment system positioned for 0° and 7° slope in use.

The tibial alignment jig 5 has a sliding rail 6. The sliding rail 6 is adapted to be connected to a head of the tibia 2 at its proximal end portion. The sliding rail 6 is connected to a sliding rail fix 7, which can be inserted into the tibia 2, in particular the tibia head, or adjusted to an element, which is inside the tibia 2. Alternatively, the sliding rail fix 7 is a stylus and provides correct positioning of the sliding rail 6, and thus the tibial alignment jig 5.

The tibial alignment jig 5 has a casing 8. The casing 8 slidably receives (a distal end portion of) the sliding rail 6 along a sliding axis S. The sliding axis S corresponds to a longitudinal axis of the sliding rail 6. The casing 8 is attached to the alignment rod 3 via a pivoting axis P such that the alignment rod 3 and the sliding rail 6 are kept pivotable to each other. The pivoting axis P is perpendicular to the sliding axis S.

The tibial alignment jig 5 has a user adjustment element 9. The user adjustment element 9 is rotatably held by the alignment rod 3 around a rotational axis R. The rotational axis R corresponds to a longitudinal axis of the alignment rod 3. The rotational axis R is perpendicular to the sliding axis S. The rotational axis R is perpendicular to the pivoting axis P. The user adjustment element 9 is functionally connected to the casing 9 such that a rotation of the user adjustment element 9 relative to the alignment rod 3 is converted into a pivoting movement of the alignment rod 3 relative to the sliding rail 6. The conversion of the movements is explained with reference to FIG. 2 below.

The user adjustment element 9 and the alignment rod 3 are adapted to interlock with each other at a plurality of rotational positions/locking positions of the user adjustment element 9. The plurality of rotational positions correspond to different orientations of the alignment rod 3 in accordance with the pivoting movement of the alignment rod 3, that is, to different posterior resected slopes relative to the tibia 2 guided by the alignment system 1. In FIG. 1, the alignment system 1 is aligned such that a 0° slope (left side) and a 7° slope (right side) relative to the tibia 2 can be achieved by resection.

The alignment system 1 has a tibial adjustment housing 10. The tibial adjustment housing 10 is connected to a distal end portion of the alignment rod 3. The tibial adjustment housing 10 is connected to the alignment rod 3 distal to the tibial alignment jig 5. The tibial adjustment housing 10 connects the alignment rod 3 with the tibial resection guide 4. The tibial adjustment housing 10 is slidably attached to the alignment rod 3, slidable along/parallel to the rotational axis R.

Figure 2:
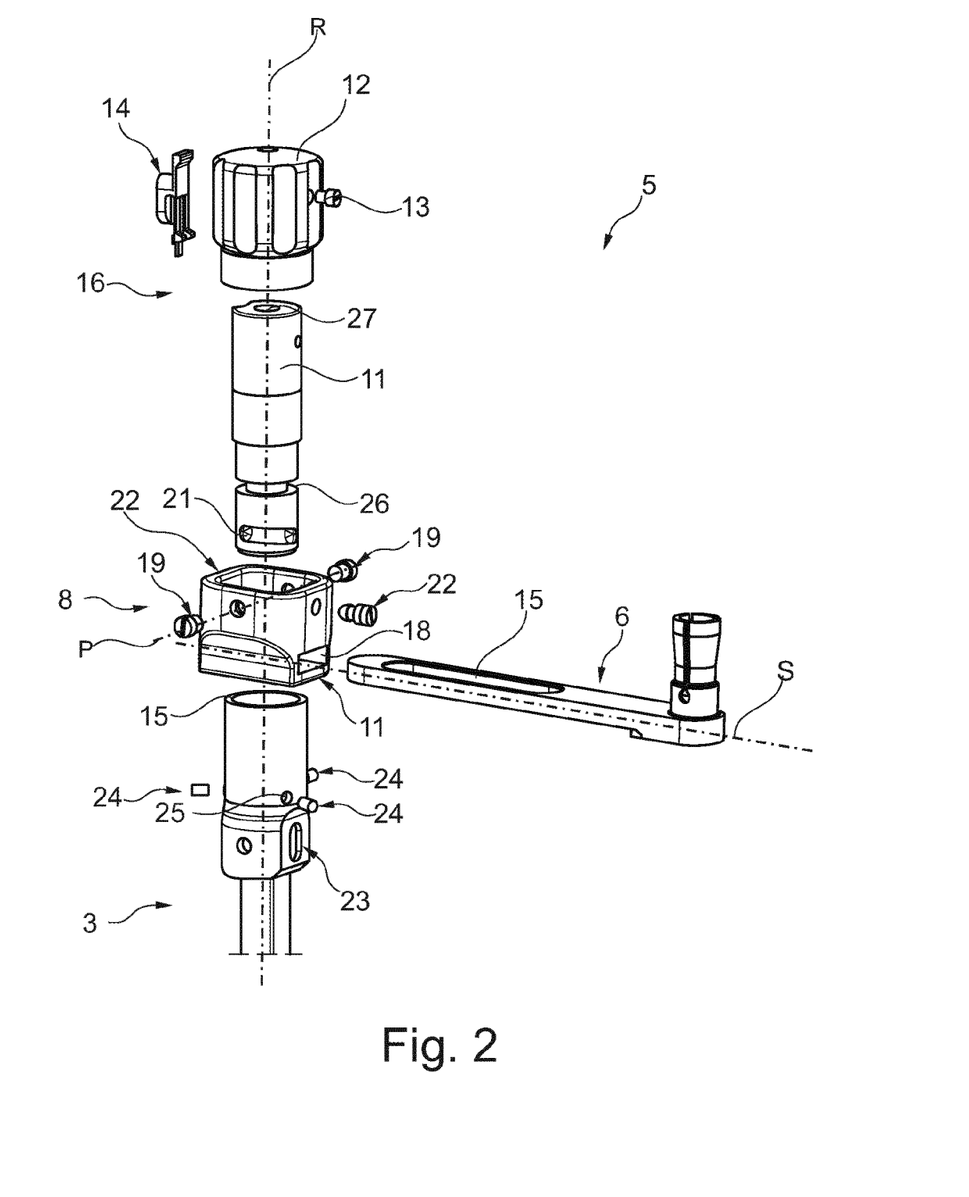
FIG. 2 illustrates an exploded view of a tibial alignment jig of the intramedullary tibia alignment system.
Figure 3:
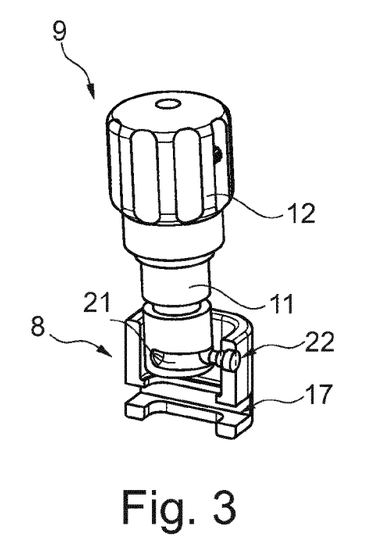
FIG. 3 illustrates a perspective view of a user adjustment element and a casing of the tibial alignment jig.
Figure 4:
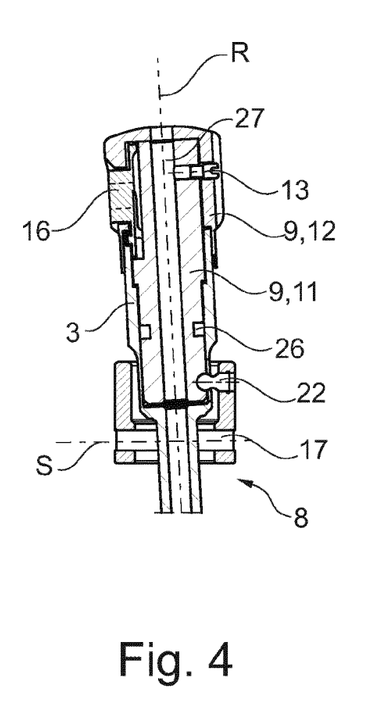
FIG. 4 illustrates a longitudinal sectional view of the user adjustment element and the casing.

FIGS. 2 to 4 show the tibial adjustment jig 5 in detail. The user adjustment element 9 comprises a (lower/distal) cylindrical support 11 and a (upper/proximal) knob portion 12. The knob portion 12 is adapted to be touched/handled by the user to adjust the alignment system 1. The cylindrical support 11 and the knob portion 12 are fixed to each other by a screw 13 engaging with the cylindrical support 11 and the knob portion 12. The cylindrical support 11 and the knob portion 12 are not movable to each other.

The alignment system 1 has a locking mechanism adapted to lock and unlock rotatable movement between the alignment rod 3 and the user adjustment element 9. The locking mechanism comprises a release element 14 and an engaging element 15. The release element 14 is fixed to the user adjustment element 9. The engagement element 12 fixed to the alignment rod 3. The release element 14 and the engaging element 15 are engaging in a locking position. The locking mechanism comprises a plurality of engaging elements 15 each forming a locking position. The plurality of engaging elements 15 are distanced from each other such that two adjacent locking positions generate a constantly stepwise, more preferably in 1° steps, pivoting movement between the alignment rod 3 and the sliding rail 6. The release element 14 comprises a button 16 on a circumference of the user adjustment element 9. The button 16 is adapted to be pressed manually by a user to unlock the locking mechanism and to enable the user adjustment element 9 to be turned in clockwise or anti-clockwise in circumferential direction relative to the alignment rod 3. Without pressing the button 16, the user cannot turn the user adjustment element 9 in any direction. The locking mechanism is explained in detail with reference to FIG. 5 below.

The casing 8 comprises a sliding guiding slot 17. The sliding guiding slot 17 slidably receives/supports the sliding rail 6 along the sliding axis S. The sliding guiding slot 17 is formed as a through hole. The sliding guiding slot 17 has a rectangular cross section, viewed perpendicular to the sliding axis S. The sliding guiding slot 17 guides the sliding rail 6 one-directionally.

The sliding rail 6 is accommodated in the sliding guiding slot 17. The sliding rail 6 comprises an elongated hole 18. The hole 18 is elongated along the sliding axis S. The alignment rod 3 (or an element fixed to the alignment rod 3) passes through the hole 18, independent from the (sliding) position of the sliding rail 6 along the sliding axis S or from the (pivoting) position of the alignment rod 3 via the pivoting axis P.

The casing 8 comprises a pivoting element 19. The pivoting element 19 attaches the casing 8 pivotably to the alignment rod 3 via the pivoting axis P. The pivoting element 19 contacts a circumferential surface of the user adjustment element 9 (here the cylindrical support 11). The pivoting element 19 is fixed to the casing 8. The pivoting element 19 is proximal to/above the sliding guiding slot 17. The pivoting element 19 is fixed to an inner side of the casing 8 to extend towards the circumferential surface of the user adjustment element 9. The pivoting element 19 passes through a hole 20 in the alignment rod 3. The pivoting element 19 is formed by two (first) pins. The longitudinal axes of the pins each corresponds to the pivoting axis P. The pins are arranged on circumferentially opposite sides of the user adjustment element 9.

The user adjustment element 9 comprises a pivoting guiding groove 21 in a circumferential surface of the user adjustment element 9. The pivoting guiding groove 21 receives a link member 22. The link member 22 functionally connects the casing 8 and the alignment rod 3. The link member 22 is fixed at the inner side of the casing 8 and extends towards the pivoting guiding groove 21. The link member 22 is proximal to/above the sliding guiding slot 17. The pivoting guiding groove 21 is designed to cause a relative movement of the casing 8 relative to the user adjustment element 9 in case the user adjustment element 9 is rotated. For example, the casing 8 can be pulled/drawn to the user adjustment element 9 or pushed away. The link member 22 is formed as a screw or (spherical) pin. The link member 22 passes through a hole 23 in the alignment rod 3. The hole 23 is elongated along the rotational axis R. The pivoting guiding groove 21 has a helical form. That is, the pivoting guiding groove 21 is inclined to the circumferential direction causing a relative movement of the casing 8 relative to the user adjustment element 9 in case a spherical axis of the link member 22 is guided in the pivoting guiding groove 21 in the circumferential direction. Alternatively, the pivoting guiding groove 21 can have a depth (constantly) increasing or decreasing along its circumferential extension to cause the relative movement of the casing 8 relative to the user adjustment element 9. The circumferential extension of the pivoting guiding groove 21 can provide a limit stop for the rotational movement of the user adjustment element 5 relative to the alignment rod 3.

The alignment system 1 comprises a fastening element 24. The fastening element 24 rotatably attaches the user adjustment element 9 to the alignment rod 3 along the rotational axis R. The fastening element 24 is fixed to the alignment rod 3 (the fastening element 24 engages with holes 25 in the alignment rod 3). The fastening element 24 is formed by a plurality of (second) pins, here three second pins. The longitudinal axes of the pins are perpendicular to the rotational axis R.

The pins are spaced in a circumferential direction of the user adjustment element 9. The pins are spaced in equal distances to each other. The user adjustment element 9 comprises a groove 26 in a circumferential surface of the user adjustment element 9 extending in a plane perpendicular to the rotational axis R. The groove 26 is formed circumferentially. The groove 26 receives the fastening element 26 (the pins).

The tibial alignment jig 2 comprises a through hole 27 extending through the alignment system 1. The through hole 27 corresponds/extends parallel to the rotational axis R. The through hole 27 is adapted to receive/accommodate a separate extramedullary check rod 28 (see FIG. 1) for verifying the adjusted slope of the alignment rod 3 to the tibia 2. Alternatively, the alignment rod 3 can be formed by a telescopic extending bar being adjustable in length. The portion of the bar extending proximally from the tibial alignment jig 2 can be used as the extramedullary check rod.

Figure 5:
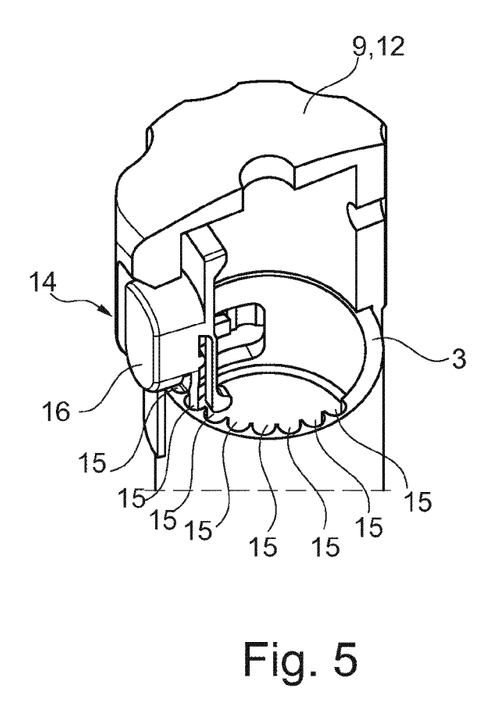
FIG. 5 illustrates a perspective view of a locking mechanism of the user adjustment element shown partially longitudinally sectioned.

FIG. 5 shows the looking mechanism in detail. The release element 14 is formed or has a snap-fit hook. The engaging element 15 is formed or has snap-fit slot. The snap-fit slot is formed at the inner (circumferential) side of the alignment rod 3 (or of an element fixed to the alignment rod 3). The snap-fit hook extends towards the inner (circumferential) side of the alignment rod 3 and engages with (one of) the snap-fit slot(s) in the locking/locked position. Pushing the button 16 towards a radially inner direction (for example, against the force of a spring) releases the snap-fit between the hook and the slot such that the turning the user adjustment element 9 is enabled. The snap-fit slots are distanced in circumferential direction of the alignment rod 3. The circumferential distance between adjacent locking positions generates a defined step of the pivoting movement between the alignment rod 3 and the sliding rail 6, and thus the tibia 2.

The invention claimed is:

1. An intramedullary tibia alignment system for aligning a cutting instrument, the cutting instrument being a proximal tibial resection cutting instrument, the intramedullary tibia alignment system having an alignment rod for adjusting the alignment system individually to a tibia, a tibial resection guide for guiding the cutting instrument and being connected to a proximal end portion of the alignment rod and a tibial alignment jig for orientating the tibial resection guide relative to the tibia and being connected to the alignment rod proximal to the tibial resection guide, wherein the tibial alignment jig has a sliding rail adapted to be connected to a head of the tibia at a proximal end portion, and a casing slidably receiving the sliding rail along a sliding axis, wherein the casing is attached to the alignment rod via a pivoting axis such that the alignment rod and the sliding rail are kept pivotable to each other, and the tibial alignment jig further comprises a user adjustment element rotatably held by the alignment rod around a rotational axis and functionally connected to the casing by a link element such that a rotation of the user adjustment element relative to the alignment rod is converted into a pivoting movement of the alignment rod relative to the sliding rail, wherein the user adjustment element and the alignment rod are adapted to interlock with each other at a plurality of rotational positions of the user adjustment element, said plurality of rotational positions corresponding to different orientations of the alignment rod in accordance with the pivoting movement of the alignment rod.

2. The intramedullary tibia alignment system according to claim 1, further comprising a locking mechanism adapted to lock and unlock rotatable movement between the alignment rod and the user adjustment element, the locking mechanism comprising a release element fixed to the user adjustment element and an engaging element fixed to the alignment rod, the release element engaging with the engaging element in a locking position.

3. The intramedullary tibia alignment system according to claim 2, wherein the locking mechanism comprises a plurality of engaging elements each forming a locking position, the plurality of engaging elements being distanced from each other.

4. The intramedullary tibia alignment system according to claim 2, wherein the release element comprises a button on a circumference of the user adjustment element, the button being adapted to be pressed manually by a user to unlock the locking mechanism and to enable the user adjustment element to be turned clockwise or counter-clockwise in a circumferential direction of the alignment rod.

5. The intramedullary tibia alignment system according to claim 1, wherein the casing comprises a sliding guiding slot slidably receiving the sliding rail along the sliding axis, the sliding axis being a longitudinal direction of the sliding rail.

6. The intramedullary tibia alignment system according to claim 5, wherein the sliding rail comprises a hole elongated along the sliding axis through which the alignment rod passes.

7. The intramedullary tibia alignment system according to claim 1, wherein the casing comprises a pivoting element attaching the casing pivotably to the alignment rod via the pivoting axis, the pivoting axis being perpendicular to the rotational axis and perpendicular to the sliding axis.

8. The intramedullary tibia alignment system according to claim 1, wherein the user adjustment element comprises a pivoting guiding groove in a circumferential surface of the user adjustment element receiving the link element, the link element being fixed at an inner side of the casing and extending towards the pivoting guiding groove, the pivoting guiding groove configured to cause a relative movement of the casing relative to the user adjustment element when the user adjustment element is rotated.

9. The intramedullary tibia alignment system according to claim 8,
wherein the pivoting guiding groove has a depth that increases or decreases along its circumferential extension, or
wherein the pivoting guiding groove has a helical form.

10. The intramedullary tibia alignment system according to claim 1, further comprising a fastening element for rotatably attaching the user adjustment element to the alignment rod along the rotational axis, the rotational axis being a longitudinal direction of the alignment rod, the user adjustment element comprising a groove in a circumferential surface of the user adjustment element extending in a plane perpendicular to the rotational axis receiving the fastening element being fixed to the alignment rod.

11. The intramedullary tibia alignment system according to claim 1, wherein the alignment rod is a telescopic extending bar being adjustable in length or the alignment rod and the user adjustment element each forming a through hole extending along the rotational axis, the through hole adapted to receive an extramedullary check rod.

12. The intramedullary tibia alignment system according to claim 1, further comprising a tibial adjustment housing holding the alignment rod and connecting the alignment rod and the tibial alignment jig with the tibial resection guide.

13. The intramedullary tibia alignment system according to claim 12, wherein the tibial adjustment housing is slidably attached to the alignment rod along the rotational axis.

* * * * *